(12) United States Patent
Meyer et al.

(10) Patent No.: US 10,441,327 B2
(45) Date of Patent: Oct. 15, 2019

(54) INSTRUMENT AND METHOD FOR IN SITU ROD ADJUSTMENT

(71) Applicant: Alphatec Spine, Inc., Carlsbad, CA (US)

(72) Inventors: Nathan Meyer, Vista, CA (US); Martin Bouliane, Carlsbad, CA (US); Wally Gillespie, Carlsbad, CA (US); Anand Parikh, San Diego, CA (US); Jens Peter Timm, Carlsbad, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 47 days.

(21) Appl. No.: 15/626,452

(22) Filed: Jun. 19, 2017

(65) Prior Publication Data

US 2017/0281240 A1    Oct. 5, 2017

Related U.S. Application Data

(62) Division of application No. 14/068,416, filed on Oct. 31, 2013, now Pat. No. 9,707,018.

(60) Provisional application No. 61/722,993, filed on Nov. 6, 2012.

(51) Int. Cl.
*A61B 17/70* (2006.01)
(52) U.S. Cl.
CPC ...... *A61B 17/7083* (2013.01); *A61B 17/7032* (2013.01); *A61B 17/7037* (2013.01)
(58) Field of Classification Search
CPC ............ A61B 17/7032; A61B 17/7034; A61B 17/7074–7089; A61B 17/701; A61B 17/7011; A61B 17/7014; A61B 17/8869; A61B 17/8872; A61B 17/88
See application file for complete search history.

(56) References Cited

U.S. PATENT DOCUMENTS

| | | | |
|---|---|---|---|
| 6,517,544 B1 | 2/2003 | Michelson | |
| 7,204,023 B2 | 4/2007 | Chang | |
| 8,590,163 B1 | 11/2013 | Bagley et al. | |
| 8,870,886 B2 | 10/2014 | Burgi | |
| 2005/0086811 A1 | 4/2005 | Kawasaki | |
| 2006/0229627 A1 | 10/2006 | Hunt et al. | |
| 2007/0270867 A1 | 11/2007 | Miller et al. | |
| 2009/0054902 A1* | 2/2009 | Mickiewicz | A61B 17/701 606/103 |
| 2012/0083657 A1 | 4/2012 | Roth et al. | |
| 2012/0197318 A1 | 8/2012 | Barry et al. | |
| 2013/0345759 A1* | 12/2013 | Meyer | A61B 17/7074 606/279 |
| 2014/0128930 A1* | 5/2014 | Meyer | A61B 17/7083 606/86 A |

(Continued)

*Primary Examiner* — Ellen C Hammond
*Assistant Examiner* — Tessa M Matthews
(74) *Attorney, Agent, or Firm* — Honigman LLP (57) ABSTRACT

The instruments and methods of the present disclosure include an outer shaft, an inner shaft, a roller, and an actuator. In some examples, the outer shaft includes a lumen extending from a proximal end to a distal end. The inner shaft is disposed within the lumen. The roller rotatably is coupled with the distal end at an axis and configured to engage the fixation rod. The actuator operably couples with the inner shaft to translate the inner shaft within the lumen and cause rotation of the roller to impart linear movement on the fixation rod.

19 Claims, 9 Drawing Sheets

(56) References Cited

U.S. PATENT DOCUMENTS

| | | | |
|---|---|---|---|
| 2015/0018892 A1* | 1/2015 | Lindner | A61B 17/7083 |
| | | | 606/86 A |
| 2015/0313642 A1* | 11/2015 | Fessler | A61B 17/701 |
| | | | 606/258 |
| 2016/0038197 A1* | 2/2016 | Semingson | A61B 17/708 |
| | | | 606/86 A |
| 2017/0095275 A1* | 4/2017 | Lynch | A61B 17/7014 |

* cited by examiner

INSTRUMENT AND METHOD FOR IN SITU ROD ADJUSTMENT

CROSS-REFERENCE TO RELATED APPLICATIONS

The present application is a divisional application of U.S. application Ser. No. 14/068,416 filed on Oct. 31, 2013, which in turn claims priority to U.S. Provisional Application Ser. No. 61/722,993 entitled "Rod Pusher and Methods of Use" which was filed on Nov. 6, 2012, both of which are incorporated herein by reference in their entirety.

FIELD

The present disclosure relates generally to spinal orthopedics, and more particularly to systems and methods for adjusting a spinal fixation rod percutaneously and in situ.

BACKGROUND

The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies. Various spinal disorders may cause the spine to become misaligned, curved, and/or twisted or result in fractured and/or compressed vertebrae. It is often necessary to surgically correct these spinal disorders.

The spine includes seven cervical (neck) vertebrae, twelve thoracic (chest) vertebrae, five lumbar (lower back) vertebrae, and the fused vertebrae in the sacrum and coccyx that help to form the hip region. While the shapes of individual vertebrae differ among these regions, each is essentially a short hollow shaft containing the bundle of nerves known as the spinal cord. Individual nerves, such as those carrying messages to the arms or legs, enter and exit the spinal cord through gaps between vertebrae.

The spinal disks act as shock absorbers, cushioning the spine, and preventing individual bones from contacting each other. Disks also help to hold the vertebrae together. The weight of the upper body is transferred through the spine to the hips and the legs. The spine is held upright through the work of the back muscles, which are attached to the vertebrae. While the normal spine has no side-to-side curve, it does have a series of front-to-back curves, giving it a gentle "S" shape. If the proper shaping and/or curvature are not present due to scoliosis, neuromuscular disease, cerebral palsy, or other disorder, it may be necessary to straighten or adjust the spine into a proper curvature.

Generally the correct curvature is obtained by manipulating the vertebrae into their proper position and securing that position with a rigid system of screws, rods, intervertebral spaces, and/or plates. The various components of the system may be surgically inserted through open or minimally invasive surgeries. The components may also be inserted through various approaches to the spine including anterior, lateral, and posterior approaches and others in between.

Spinal fixation systems may be used in surgery to align, adjust, and/or fix portions of the spinal column, i.e., vertebrae, in a desired spatial relationship relative to each other. Many spinal fixation systems employ a spinal fixation rod for supporting the spine and for properly positioning components of the spine for various treatment purposes. Vertebral anchors, comprising pins, bolts, screws, and hooks, engage the vertebrae and connect the fixation rod to different vertebrae. The size, length, and shape of the cylindrical rod depend on the size, number, and position of the vertebrae to be held in a desired spatial relationship relative to each other by the apparatus.

During spinal surgery, a surgeon first exposes the spine posterior and attaches the vertebral anchors to selected vertebrae of the spine. The surgeon then inserts a properly shaped spinal rod into rod-receiving portions of the vertebral anchors to connect the selected vertebrae, thereby fixing the relative positions of the vertebrae. Generally, a controlled mechanical force is required to bring together the spinal rod and a spinal implant, such as the vertebral anchors, in a convenient manner. After insertion, a surgeon must insert a locking mechanism, such as a set screw, into the vertebral anchor to lock the spinal rod to the implant after the force for inserting the rod is removed.

In some surgeries, the surgeon may utilize a minimally invasive approach in which small incisions are made and through which the screws and rods are inserted. Often the stabilization rods may inserted through one of the surgical entry points used to insert a screw. Accurate and precise placement of the stabilization rod in the receivers of the screws may be difficult to achieve. Due to the minimally invasive approach, the rod may require adjustment in situ. The present invention attempts to solve these problems as well as others.

SUMMARY

Accordingly, the instruments and methods of the present disclosure include an outer shaft, an inner shaft, a roller, and an actuator. In some examples, the outer shaft includes a lumen extending from a proximal end to a distal end. The inner shaft is disposed within the lumen. The roller rotatably is coupled with the distal end at an axis and configured to engage the fixation rod. The actuator operably couples with the inner shaft to translate the inner shaft within the lumen and cause rotation of the roller to impart linear movement on the fixation rod.

In other features, a connecting rod links a distal end of the inner shaft with an off-axis point of the roller. A slot on the distal end of the outer shaft receives the axis of the roller and allows the roller to translate distally and proximally from the fixation rod. A handle fixedly coupled with the proximal end of the outer shaft and a lever pivotally coupled with the handle shaft and linked to the inner shaft by a lever connector.

In still other features, the roller comprises a pair of rollers. The roller includes a friction-enhancing surface. The roller includes a serrated surface.

In yet other features, the actuator is advanced to a drive position in which the inner shaft advances distally causing increased friction between the roller and the fixation rod. A spring that returns the actuator to a rest position in which the inner shaft is drawn proximally. The actuator advances the inner shaft distally causing the roller to rotate and impart a force to translate the fixation rod.

The instrument may be used for advancing an in situ fixation rod relative to an implanted screw assembly in a method comprising the steps of inserting the instrument, positioning the actuator to impart linear movement on the inner shaft to engage the roller with the fixation rod in a drive position, and positioning the actuator to impart linear movement on the inner shaft to rotate the roller while engaged with the fixation rod.

In still other features, the method includes positioning the actuator to impart linear movement on the inner shaft that increases friction between the roller and the fixation rod and positioning the actuator to impart linear movement on the inner shaft that disengages the roller from the fixation rod.

DETAILED DESCRIPTION

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

The present disclosure relates to instruments and methods for advancing a fixation rod in situ and percutaneously as in a minimally invasive spinal surgery. In some examples, the instrument may be referred to as a rod pusher in that the instrument "pushes" the rod into position within one or more rod-receiving members of a screw assembly such as a body member of a polyaxial screw assembly. Although the examples provide herein generally refer to polyaxial screws, fixed screws, monoaxial screws, and uni-planar screws are all contemplated as they all generally include a rod-receiving member on proximal ends of the screw assemblies. The rod pusher may operably couple to a screw assembly to move, translate, or displace the fixation rod. The rod pusher may generally be used to move, translate, or displace any instrument or device that may be required to move along an axis.

Figure 1:
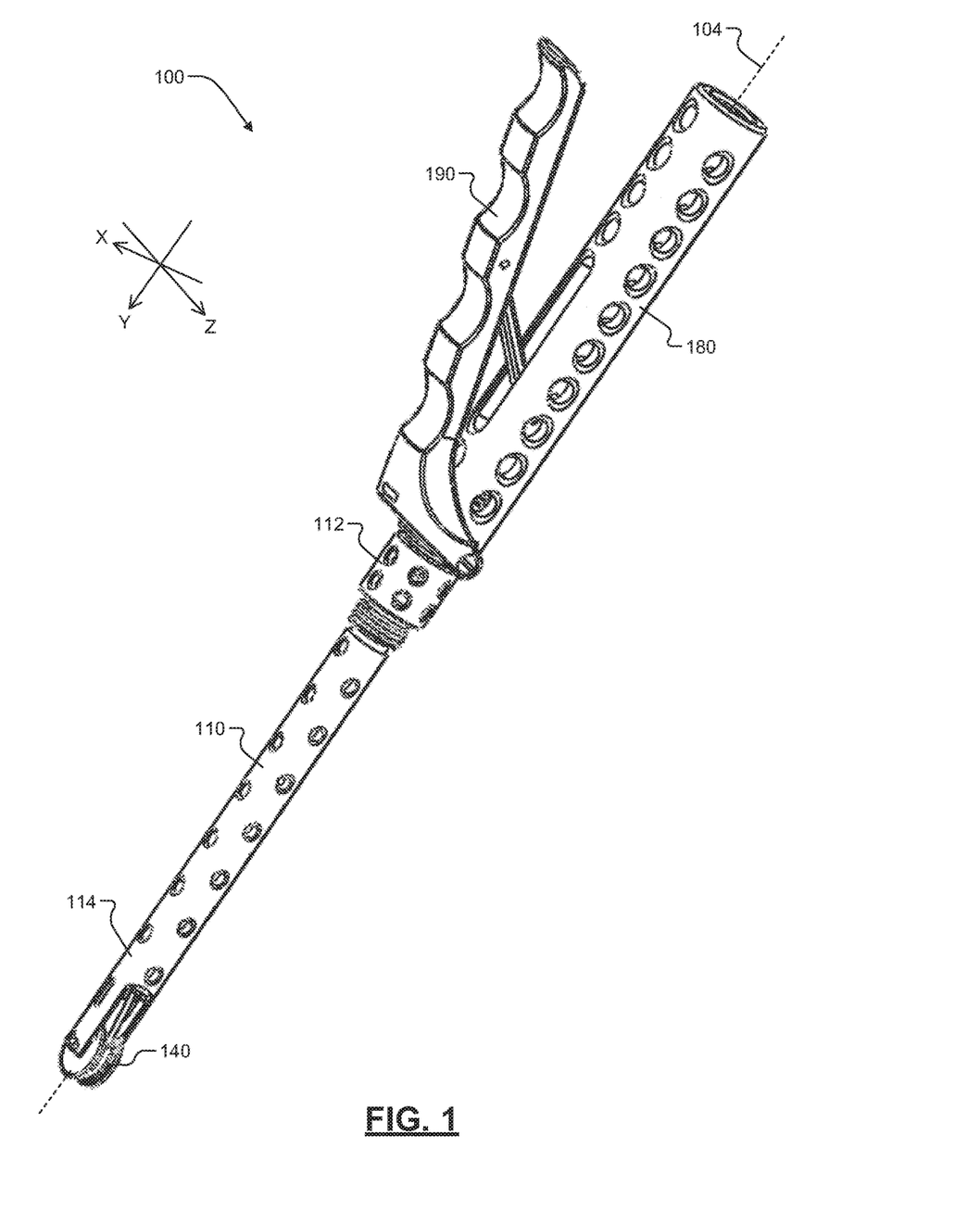
FIG. 1 is a perspective view of an exemplary instrument for in situ rod adjustment according to the principles of the present disclosure.

As shown in FIG. 1, the rod pusher 100 generally comprises an outer shaft 110 including a proximal end operably coupled to a handle 180 and a lever 190. The outer shaft 110 extends along a generally longitudinal axis 104 of the rod pusher 100, wherein the outer shaft 110 includes a proximal end 112 and a distal end 114 generally along the longitudinal axis 104. The longitudinal axis 104 is generally shown along the y-axis. The distal end 114 of the outer shaft 110 is operably coupled with at least one roller 140, which operates to conform or couple with a fixation rod, as further detailed below. The proximal end 112 of the outer shaft 110 is operably coupled with the handle 180 and the lever 190 to rotate the at least one roller 140 and operably move the fixation rod coupled with or engaged with the roller 140. In one embodiment, the roller 140 operably moves the fixation rod substantially along the z-axis or cranial-caudal direction 106, alternatively the roller 140 may operably move the fixation rod substantially along the along the x-axis or y-axis. In one embodiment, the roller 140 operably engages the fixation rod and moves the fixation rod along a path substantially parallel to the z-axis (and perpendicular to the longitudinal axis 104) upon operation of the lever 190 and disengages with the fixation rod upon release of the lever 190.

Figures 2A, 2B:
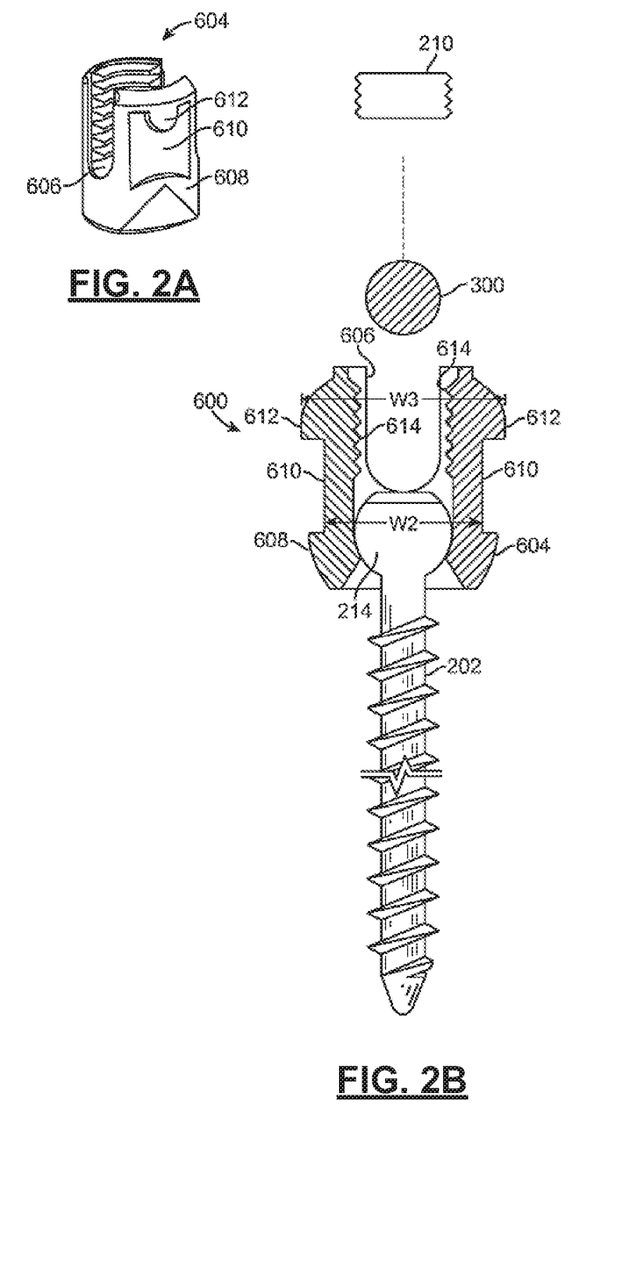
FIG. 2A is a perspective view of a head portion for an exemplary screw assembly.
FIG. 2B is a partial cross-sectional view of the screw assembly and a fixation rod.

Referring now to FIGS. 2A-2B, the rod pusher 100 is operably coupled with a head portion 604 of a screw assembly 600, which may be configured with a threaded portion 202 of the screw assembly 600 or any other screw according to the prior art. For example, the head portion 604 may couple with a rounded portion 214 on the proximal end of the threaded portion 202 in a poly-axial screw configuration. A channel 606 running through the interior of the head portion 604 is configured to receive the fixation rod 300. A projection 612 protrudes from each of the recessed surfaces 610. For example, the projection 612 may be a half-cylinder shaped projection configured to engage. The distal end 114 of the outer shaft 110 may operably couple or seat with the projections 612, such as to secure the roller 140 within the channel 606.

A width W1 is between the channel 606, which permit the roller to 140 to couple with the fixation rod 300. An outer surface 608 of the head portion 604 includes two recessed surfaces 610 that are separated by the width W2. The outer surfaces of the projections 612 may be separated by a width W3 that is greater than the width W1. Once the fixation rod 300 is seated in the channel 606, the rod pusher 100 may be engaged within the channel 606 and the roller 140 may be engaged with the fixation rod 300. After the fixation rod 300 is appropriately moved or positioned, a set screw 210 may be attached to compress the fixation rod 300 and rounded portion 214 of the threaded portion 202 together with the head portion 604. Alternatively, a bushing (not shown) may be disposed between the fixation rod 300 and the rounded portion 214 as known in the art.

Figure 3A:
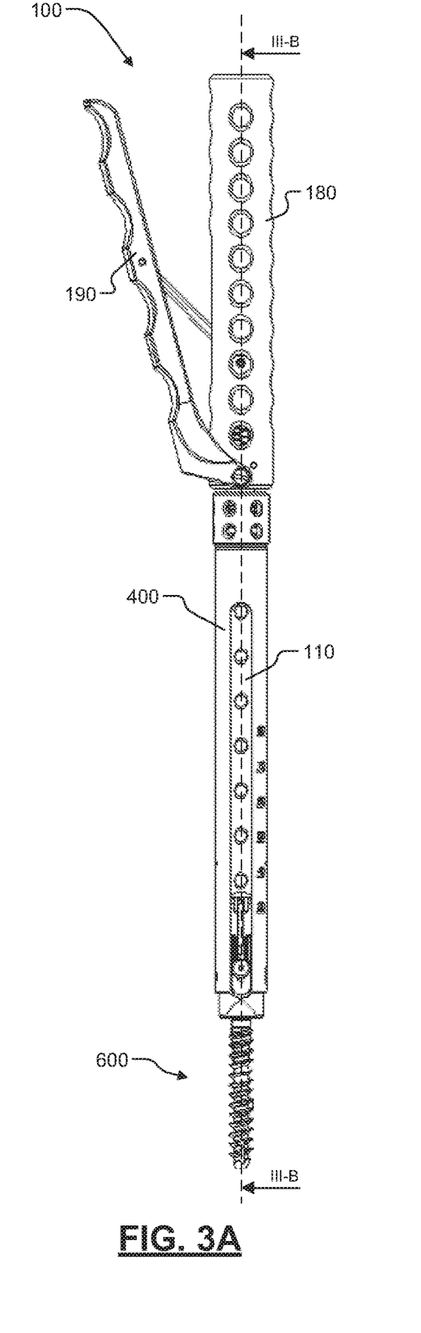
FIG. 3A is a side view of the exemplary instrument of FIG. 1 engaged with the screw assembly and fixation rod of FIG. 2B.
Figure 3B:
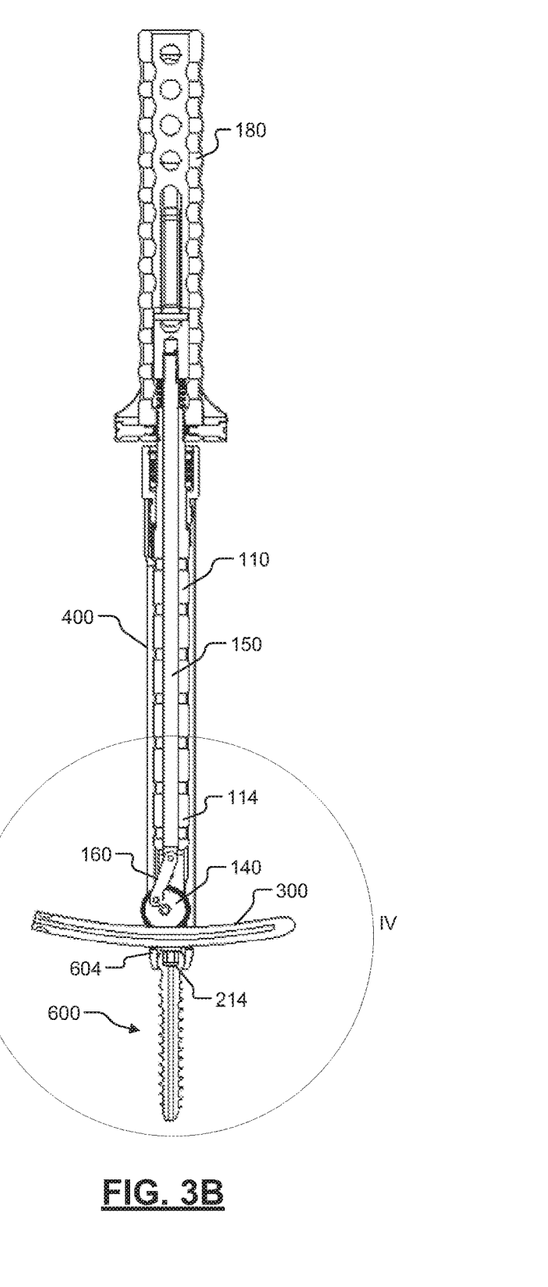
FIG. 3B is a cross sectional view in the plane III-B of FIG. 3A.

As shown in FIGS. 3A-3B, the instrument 100 may be inserted into a screw extender 400 that is attached to the screw assembly 600. The screw extender 400 may be a generally elongated tube with various openings that enable access to the screw assembly 600 through a minimally invasive surgical approach. The extender 400 may include a passageway through which the outer shaft 110 of the instrument 100 may be inserted. Examples of screw extender systems may be found in U.S. Application Publication No. 2009/0171391 which is incorporated herein by reference in its entirety.

Figure 4A:
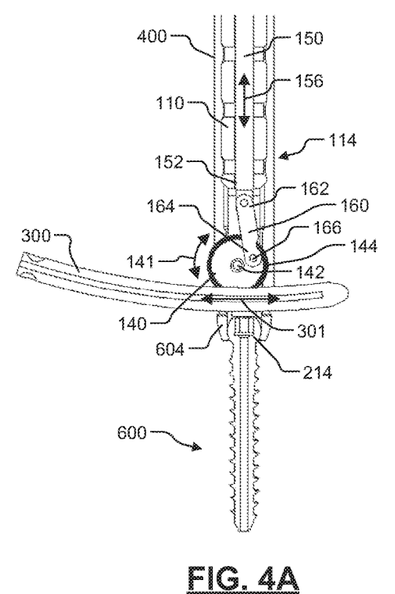
FIGS. 4A-4D are a series of sequential cross-sectional views of the distal end of the instrument engaged with the screw assembly and fixation rod and illustrating advancement of the fixation rod within the head portion by actuation of the instrument according to the principles of the present disclosure.
Figure 4B:
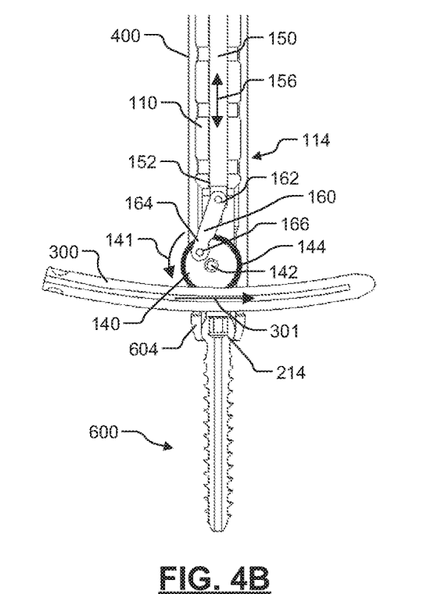
Figure 4C:
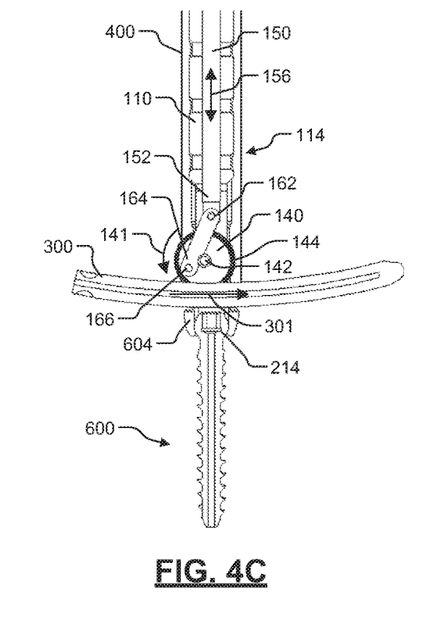
Figure 4D:
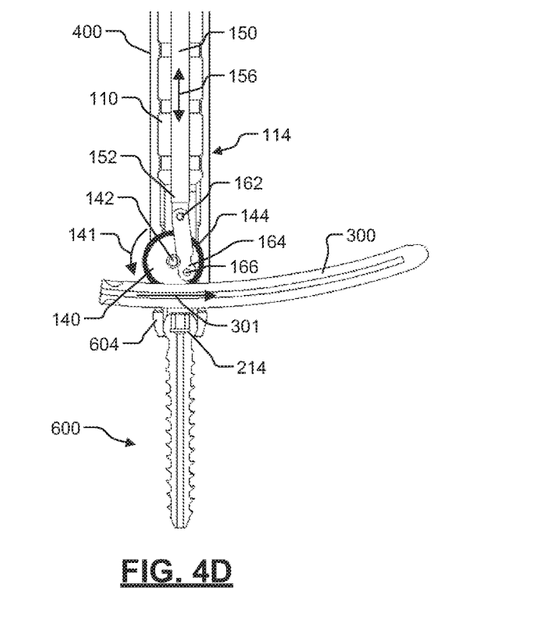

As shown in FIGS. 4A-4B, the distal end 114 of the outer shaft 110 is operably coupled to the roller 140 and the roller 140 operably engages the fixation rod 300 when the fixation rod 300 is with the channel 606 of the screw head assembly 200. A push rod 150 is coaxially coupled within the outer shaft 110; a distal end 152 of the push rod 150 is operably coupled with a proximal end 162 of the connecting rod 160. The roller 140 includes an axis 142 about which the roller 140 rotates, generally shown by arrow 141. The roller 140 may rotate clockwise or counter-clockwise. Alternately, the roller 140 may rotate in only one direction.

The connecting rod 160 is operably coupled to, engaged with, and/or in contact with a surface on the roller 140. A distal end 164 of the connecting rod 160 is rotatably coupled to an off-axis point 166 on the surface of the roller 140. The push rod 150 longitudinally moves along the longitudinal axis, shown as arrow 156, towards the distal end 114 of the outer shaft 110, which longitudinally moves the connecting rod 160 to rotationally move the roller 140 by applying a torque due to the connection at the off-axis point 166. The roller 140 is operably coupled with at least one surface of the fixation rod 300, such that the rotational movement of the roller 140 imparts force on the fixation rod 300 along the z-axis or in the general cranial-caudal direction, as shown by arrow 301. For example, the roller 140 may impart a frictional force on the rod 300.

In one embodiment, the roller 140 is not engaged with the fixation rod 300 until the push rod 150 distally displaces the connecting rod 160 as to push the roller 140 distally towards the fixation rod 300. In one embodiment, the roller 140 may disengage with the fixation rod 300 by the proximal movement of the connecting rod 160, which may proximally move the roller 140 when the lever 190 is released. In one embodiment, the connecting rod 160 and/or the roller 140 may be operably coupled with a spring as ensure pressure conformance with the fixation rod 300. In another embodiment, the roller 140 includes a plurality of serrations 144 along the outer circumference of the roller 140 as to conform to the contour of at least a portion of the surface of the fixation rod 300.

In one embodiment, the distance of the longitudinal displacement of the fixation rod 300 may be correlated to the rotations of the roller 140. For example, a larger roller 140 may be used to provide for a longer or larger longitudinal displacement of the fixation rod 300. Additionally, the fixation rod 300 may be longitudinally displaced in set or discrete increments, as determined by the roller 140 engaging, rotating, and disengaging with the fixation rod 300. The longitudinal increments may be determined by the operator, size of the roller, and the like. For example, half a rotation of the roller may correlate to a particular or discrete increment of longitudinal displacement of the fixation rod; alternatively, one-quarter of a rotation of the roller may correlate to another discrete increment of longitudinal displacement of the fixation rod.

Figure 5A:
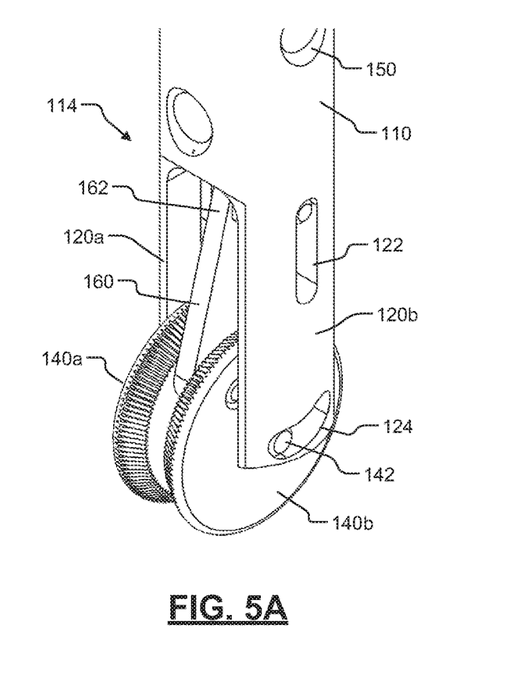
FIGS. 5A and 5B are perspective views of the distal end of the instrument according to the principles of the present disclosure.
Figure 5B:
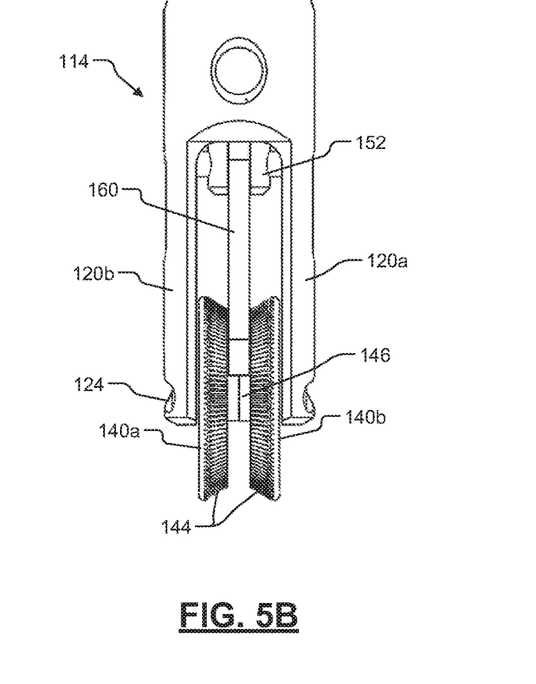

As shown in FIGS. 5A-5B, the distal end 114 of the outer shaft 110 may include a first arm 120a and a second arm 120b that project distally and operably couple the connecting rod 160 and the roller 140. The first arm 120a and second arm 120b are reciprocal in nature and mirrored components as described herein. The first arm 120a and second arm 120b include a slotted feature 122 on the proximal portion and a curved slot 124 on the distal portion of the first arm 120a and second arm 120b. The slotted feature 122 operably couples the proximal portion 162 of the connecting rod 160 to permit the connecting rod 160 to move distally. In one embodiment, the proximal portion 162 of the connecting rod 160 may be operably coupled with the slotted feature by way of a pin. The curved slot 124 operably couples the central axis 142 of the roller 140 to permit the roller 140 to move proximally and distally a small amount to disengage and engage the rod 300 and also rotate about the central axis 142. As shown in FIG. 5B, the distal end 114 may include a first roller 140a and a second roller 140b, whereby the serrations 144 face each other, or the Angle $A_s$ face each other, or towards the longitudinal axis and the first roller 140a and second roller 140b are rotatably coupled by way of corresponding central lips 146.

Figure 6A:
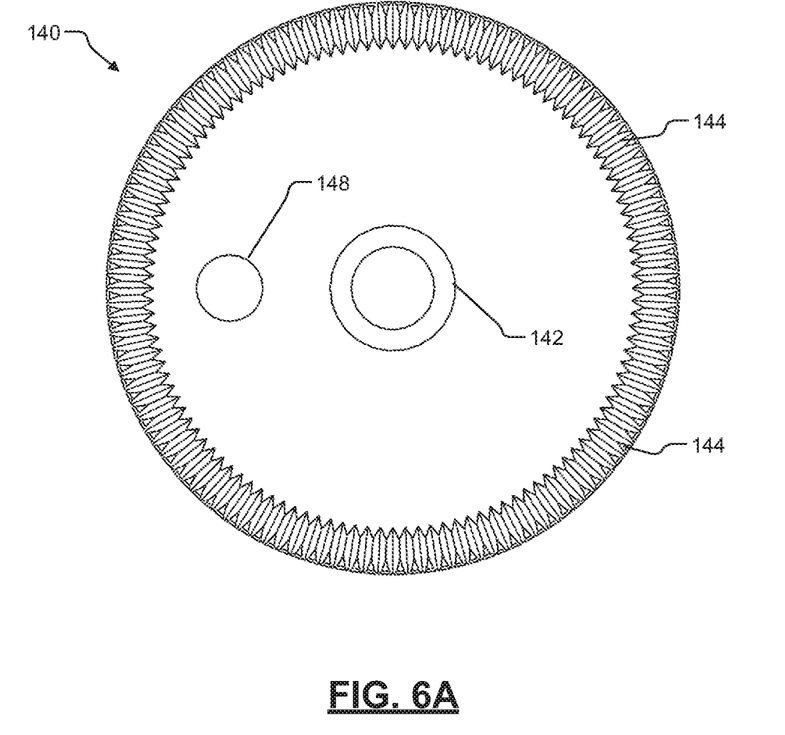
FIG. 6A is a side view of an inner face of a roller of the instrument and FIG. 6B is side view of serrations of the roller according to the principles of the present disclosure.
Figure 6B:
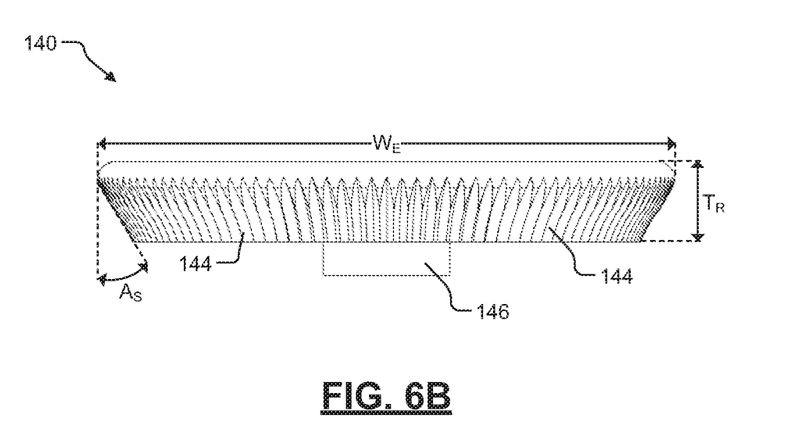

As shown in FIGS. 6A-6B, the roller 140 includes the plurality of serrations 144 along the circumference of the roller 140 and around the central axis 142. In one embodiment, the roller 140 includes a central lip 146 about to engage an adjacent roller 140 or to engage the distal end 114 of the outer shaft 110. The off-axis point 166 of engagement of the connecting rod 160 may be operably coupled to an off-axis opening 148, through which a pin or other means may rotatably couple the roller 140 to the connecting rod 160. The serrations 144 traverse at least a portion of the thickness $T_R$ of the roller 140. Although serrations 144 are shown, any other feature may be provided to increase friction forces between the roller 140 and the rod 300 so as to enhance the ability of the roller 140 to advance the rod 300. For example, various surface treatments may be used including roughening, coating, and/or rubberized layers may increase the friction forces.

The serrations 144 are set at an angle $A_s$ off of the y-axis of the roller 140, such as to permit the serrations 144 to conform to the contour of the surface of the fixation rod 300. The angle $A_s$ may be set between 0-90 degrees depending on the degree of conformation and engagement of the serrations with the surface of the fixation rod. In one embodiment, the angle $A_s$ is at least 45 degrees, which may correspond to a conformance of at least ⅛ of the exterior surface of the fixation rod. Alternatively, the serrations 144 may by curved or generally C-shaped as to conform to at least ½ of the exterior surface of the fixation rod. Alternatively, the serrations 144 may include an angle $A_s$ of between about 0-45 degrees for conformance of between about 1/10 to ⅓ of the exterior surface of the fixation rod 300. The angle $A_s$ or curvature of the serrations 144 may be adjusted depending on the degree of conformance of the serrations with the surface of the fixation rod.

Figure 7A:
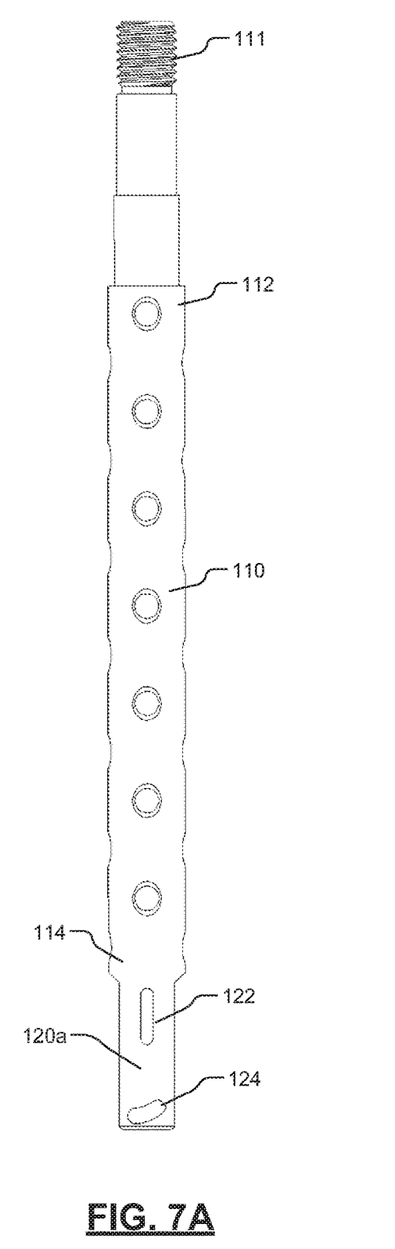
FIGS. 7A and 7B are side views of an outer shaft of the instrument according to the principles of the present disclosure.
Figure 7B:
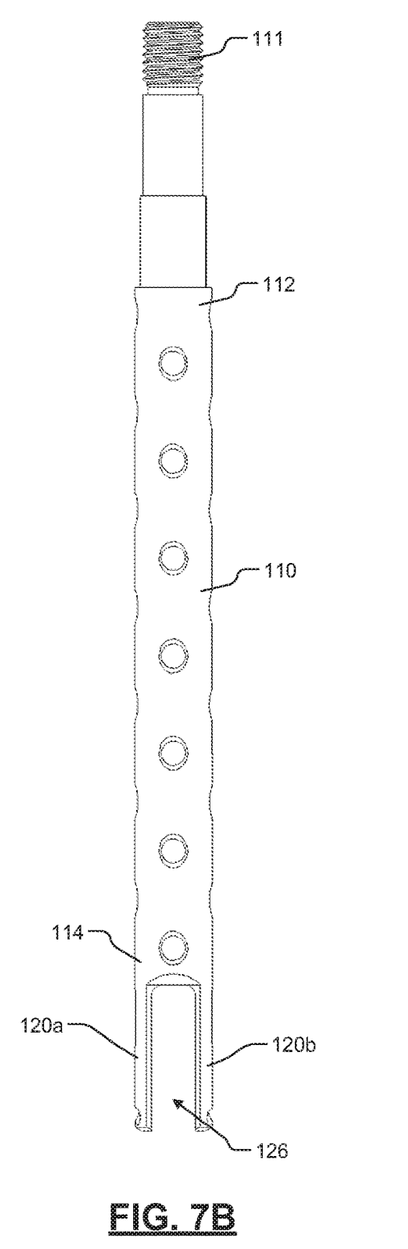
Figure 7C:
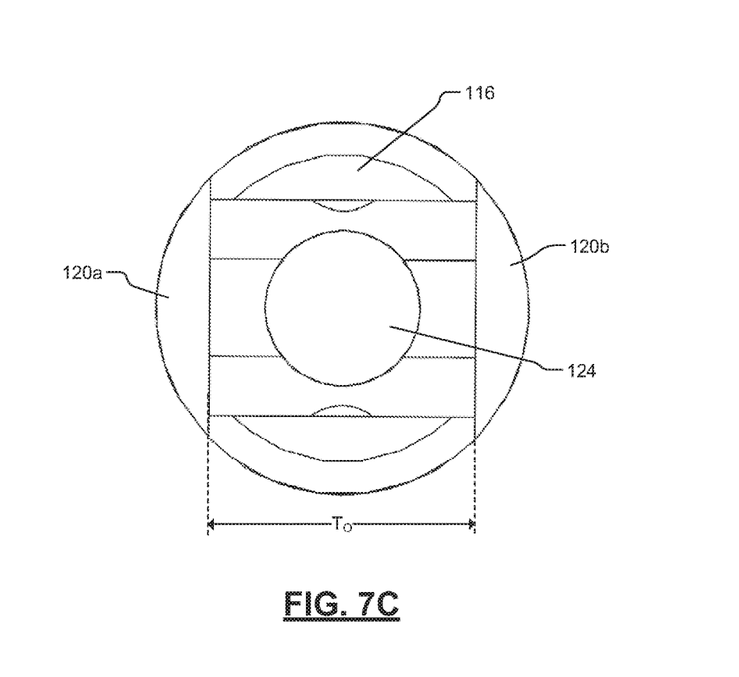
FIG. 7C is a bottom view of the outer shaft of the instrument.

As shown in FIGS. 7A-7B, the first and second arms 120a and 120b protrude from the distal end 114 of the outer shaft 110. In one embodiment, the first and second arms 120a, 120b form a roller opening 126 to position the roller 140 therebetween and permit rotation of the roller 140 between the roller opening 126. The slotted feature 122 is slotted through the thickness of the first and second arms 120a, 120b, and the curved slot 124 traverses the thickness of the first and second arms 120a, 120b. As shown in FIG. 7C, the first and second arms 120a, 120b include a generally curved outer surface, which may be complementary to at least a portion of the head portion 604. The outer shaft 110 includes a central lumen 116 traversing from the proximal end 112 to the distal end 114. The roller opening 126 generally includes thickness $T_o$, which permits the placement of at least one or two rollers 140 therebetween. The outer shaft 110 includes a threaded section 111 on the proximal end 112, as to be operably coupled to the handle 180. In one embodiment, the proximal end 112 may include a staggered section for additional securement of the proximal end 112 to the handle 180.

Figure 8:
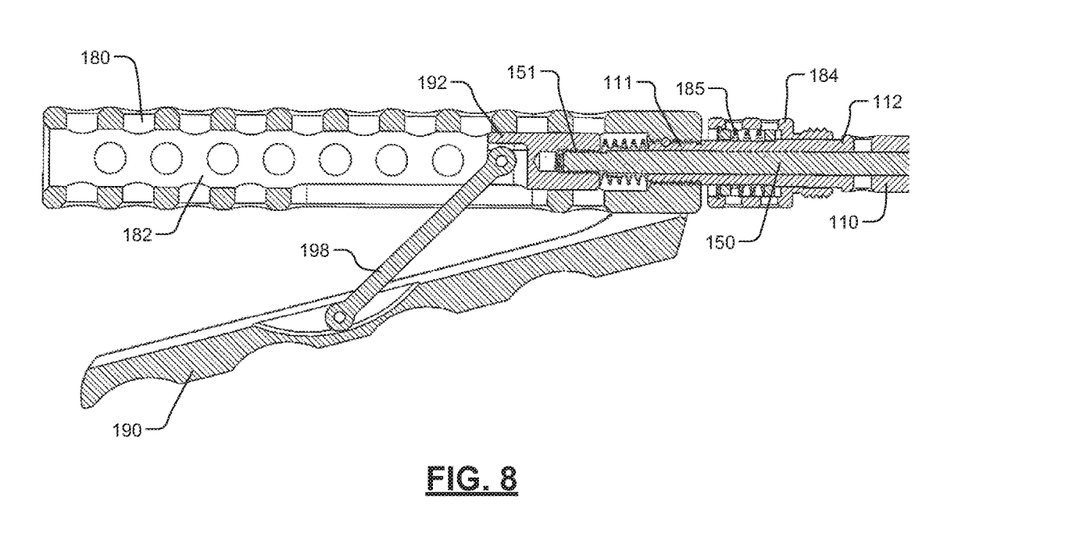
FIG. 8 is a cross-sectional view of a proximal end of the instrument according to the principles of the present disclosure.
Figure 9:
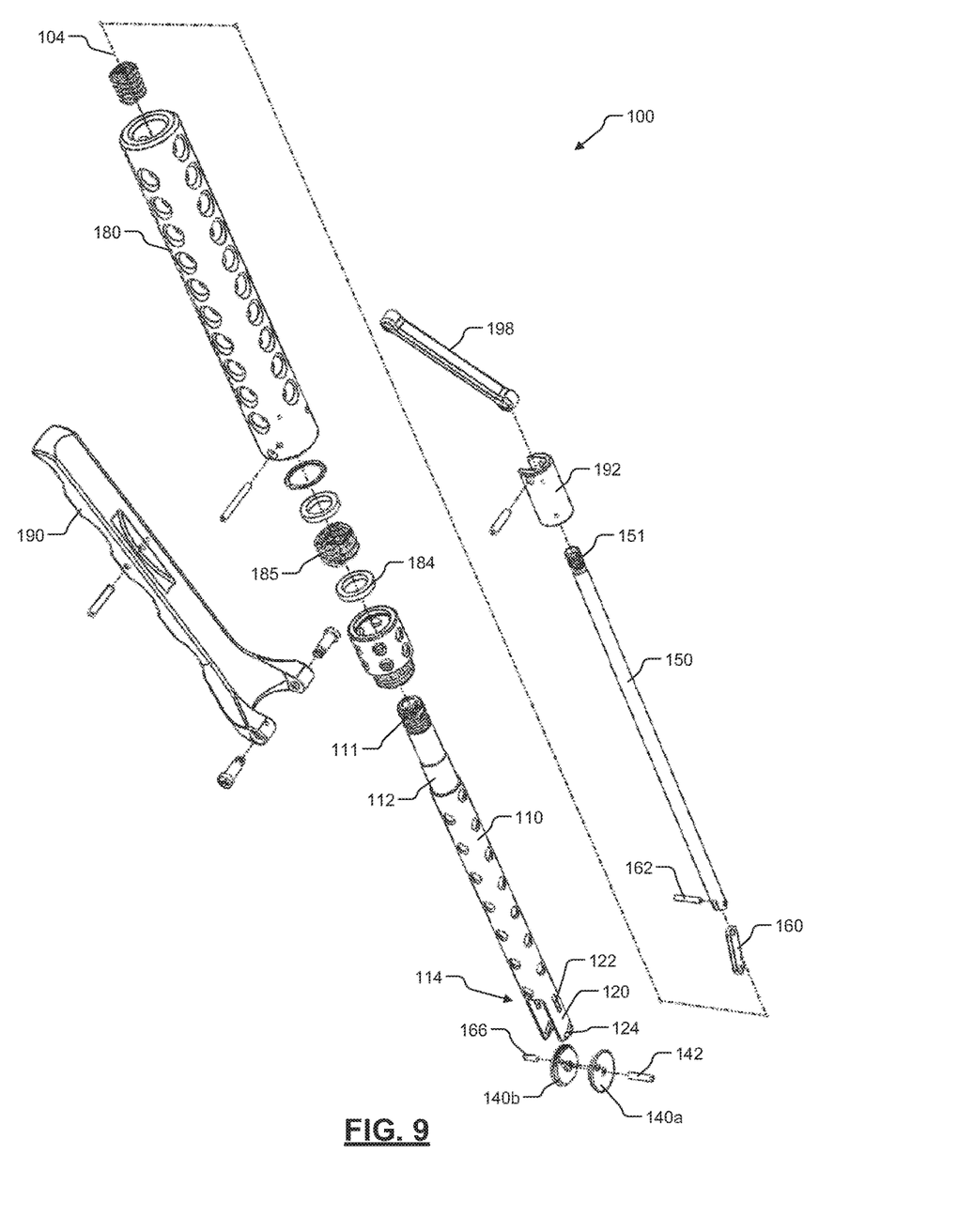
FIG. 9 is an exploded perspective view of the instrument according to the principles of the present disclosure.

As shown in FIGS. 8 and 9, the distal end of the handle 180 is operably coupled with the proximal end 112 of the outer shaft 110, with the push rod 150 coaxially disposed through the lumen of the outer shaft 110 and a lumen 182 in the handle 180. The threaded end 111 of the outer shaft 110 may threadably coupled with the distal end of the handle 180 and further secured to the distal end of the handle 180 by way of a locking cap 184 and spring 185 coaxially disposed over the proximal end 112 of the outer shaft 110. The push rod 150 may include a threaded proximal portion 151 to operably engage with a translation nut 192 coaxially disposed within the lumen 182 of the handle 180. The translation nut 192 is longitudinally displaced by a lever connector 198 that is operably connected to the lever 190.

When an operator squeezes the lever 190, the level connector 198 longitudinally displaces the translation nut 192 towards the distal end of the handle 180, thereby displacing or translating the push rod 150 connected within the handle lumen 182, and distally moving the connector rod 160 to displace the roller 140 to engage the fixation rod, rotate the roller 140 to move the fixation rod. When the handle 180 is released, the lever connector 198 moves the translation nut 192 proximally within the handle lumen 182, thereby moving the push rod 150 towards the proximal end and move the connector rod proximally to withdraw the roller 140 from the fixation rod. Optionally, a spring may be coupled with the lever connector 198 in order to return the lever 190 to its original position.

In one embodiment, the displacement of the lever 190 and translation nut 192 may be correlated to the longitudinal displacement of the push rod 150 and subsequent rotations of the roller 140. For example, if the lever 190 is displaced a larger distance, the push rod 150 may also be displaced a larger distance for a greater number of rotations of the roller 140 and longer longitudinal displacement of the fixation rod 300. Additionally, the lever 190 and the translation nut 192 may be displaced in set or discrete increments, as determined by a ratcheting or locking mechanism. The displacement increments may be determined by the operator, size of the ratchets, the locking distance, and the like. For example, the lever 190 may be only displaced towards the handle a particular or discrete distance, which would correlate to a particular or discrete displacement of the translation nut 192 and the push rod 150.

As can be understood by one skilled in the art, the rod pusher 100 and/or any of its components may have any size, shape, length, thickness, height, weight, or any other parameters. Such parameters may be selected by the surgeon (or other qualified professional) for performance of specific procedures. Further, the rod pusher 100 and/or any of its components may be manufactured from metal, plastic, synthetic material, or other suitable materials, or any combination thereof. In one embodiment, the rod pusher 100 is composed of titanium, Nitinol, or stainless steel, or any medical grade polymer, such as Polyether ether ketone (PEEK).

In some embodiments, various lengths and configurations may also include various features to accommodate different applications for the rod pusher. The rod pusher can be constructed of various materials to aid in radio translucency, strength, flexibility, and integration with anatomy, etc.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

The invention claimed is:

1. A method for advancing an in situ fixation rod relative to an implanted screw assembly, comprising:
   inserting an instrument comprising:
      an outer shaft including a lumen extending from a proximal end to a distal end of the outer shaft;
      an inner shaft within the lumen;
      a roller rotatably coupled with the distal end at an axis and configured to engage the fixation rod; and
      an actuator operably coupled with the inner shaft to translate the inner shaft within the lumen and cause rotation of the roller to impart linear movement on the fixation rod;
   positioning the actuator to impart linear movement on the inner shaft to engage the roller with the fixation rod in a drive position;
   positioning the actuator to impart linear movement on the inner shaft to rotate the roller while engaged with the fixation rod; and
   positioning the actuator to impart linear movement on the inner shaft that disengages the roller from the fixation rod.

2. The method of claim 1, further comprising positioning the actuator to impart linear movement on the inner shaft that increases friction between the roller and the fixation rod.

3. The method of claim 1, wherein the actuator comprises a handle fixedly coupled with the proximal end of the outer shaft and a lever pivotally coupled with the handle and linked to the inner shaft by a lever connector.

4. The method of claim 1, wherein the roller comprises a pair of rollers.

5. The method of claim 1, wherein the roller includes a friction-enhancing surface.

6. The method of claim 1, wherein the roller includes a serrated surface.

7. The method of claim 1, further comprising a spring that returns the actuator to a rest position in which the inner shaft is drawn proximally.

8. The method of claim 1, wherein the distal end comprises an elongated slot and a curved slot with the roller rotatably coupled at the distal end through the curved slot.

9. The method of claim 8, further comprising translating the roller distally and proximally from the fixation rod by moving the axis distally and proximally within the curved slot.

10. The method of claim 1, wherein the instrument further comprises a connecting rod linking a distal end of the inner shaft with an off-axis point on the roller and a pin coupling a proximal end of the connecting rod to an elongated slot.

11. The method of claim 10, further comprising translating the inner shaft within the lumen, wherein translation of the inner shaft causes rotation of the roller that imparts linear movement on the fixation rod.

12. A method for advancing a fixation rod relative to an implanted screw assembly, comprising:
    inserting an instrument comprising:
        an outer shaft including a lumen extending from a proximal end to a distal end of the outer shaft;
        an inner shaft within the lumen;
        a roller rotatably coupled with the distal end at an axis and configured to engage the fixation rod; and
        an actuator operably coupled with the inner shaft to translate the inner shaft within the lumen and cause rotation of the roller to impart linear movement on the fixation rod;
    positioning the actuator to impart linear movement on the inner shaft to engage the roller with the fixation rod in a drive position; and
    positioning the actuator to impart linear movement on the inner shaft to rotate the roller while engaged with the fixation rod;
    wherein the actuator is advanced to the drive position in which the inner shaft advances distally causing increased friction between the roller and the fixation rod.

13. The method of claim 12, further comprising positioning the actuator to impart linear movement on the inner shaft that disengages the roller from the fixation rod.

14. The method of claim 12, wherein the roller comprises a pair of rollers.

15. The method of claim 12, further comprising a spring that returns the actuator to a rest position in which the inner shaft is drawn proximally.

16. A method for advancing a fixation rod relative to an implanted screw assembly, comprising:
    inserting an instrument comprising:
        an outer shaft including a lumen extending from a proximal end to a distal end of the outer shaft;
        an inner shaft within the lumen;
        a roller rotatably coupled with the distal end at an axis and configured to engage the fixation rod; and
        an actuator operably coupled with the inner shaft to translate the inner shaft within the lumen and cause rotation of the roller to impart linear movement on the fixation rod;
    positioning the actuator to impart linear movement on the inner shaft to engage the roller with the fixation rod in a drive position; and
    positioning the actuator to impart linear movement on the inner shaft to rotate the roller while engaged with the fixation rod;
    wherein the actuator advances the inner shaft distally causing the roller to rotate and impart a force to translate the fixation rod.

17. The method of claim 16, further comprising positioning the actuator to impart linear movement on the inner shaft that disengages the roller from the fixation rod.

18. The method of claim 16, wherein the roller comprises a pair of rollers.

19. The method of claim 16, further comprising a spring that returns the actuator to a rest position in which the inner shaft is drawn proximally.

* * * * *